United States Patent [19]

Allen, Jr.

[11] Patent Number: 5,284,934
[45] Date of Patent: Feb. 8, 1994

[54] SYNTHESIS AND UTILIZATION OF CARBOHYDRATE-BINDING POLYMER-LECTIN CONJUGATES

[75] Inventor: Howard J. Allen, Jr., Tonawanda, N.Y.

[73] Assignee: Health Research Inc., Buffalo, N.Y.

[21] Appl. No.: 940,685

[22] Filed: Sep. 4, 1992

Related U.S. Application Data

[63] Continuation-in-part of Ser. No. 690,641, Apr. 24, 1991, abandoned.

[51] Int. Cl.[5] .............................. A61K 35/78
[52] U.S. Cl. ............................ 530/370; 530/371; 530/372; 530/373; 530/374; 530/375; 530/376; 530/377; 530/378; 530/379; 530/410; 530/417; 530/413; 530/421; 530/810; 530/812; 530/815
[58] Field of Search ............................ 530/370–379, 530/810, 812, 815, 421, 410, 413, 417; 424/400

[56] References Cited

U.S. PATENT DOCUMENTS

| | | | |
|---|---|---|---|
| 4,179,337 | 12/1979 | Davis | 530/303 |
| 4,312,944 | 1/1982 | Mattiasson | 436/538 |
| 4,496,689 | 1/1985 | Mitra | 525/54.1 |
| 4,791,192 | 12/1988 | Nakagawa et al. | 530/399 |
| 4,818,769 | 4/1989 | Nunberg | 514/2 |
| 4,882,226 | 11/1989 | Schutyser | 435/180 |
| 4,902,502 | 2/1990 | Nitecki et al. | 530/351 |

Primary Examiner—Thurman K. Page
Assistant Examiner—G. Kishore
Attorney, Agent, or Firm—Hodgson, Russ, Andrews, Woods & Goodyear

[57] ABSTRACT

The present invention provides a process for preparing a carbohydrate-binding lectin derivative for use as immune modulators or immunoconjugates. The polymer-lectin conjugate produced in accordance with the process is polyethylene glycol *Ricinus communis* agglutinin I (PEG-RCAI). The lectin is coupled to the polymer by activating the polymer with a coupling agent such as 1,1-carbonyldiimidazole. The polymer-lectin conjugate is biologically active, biocompatible and is expected to be substantially non-immunogenic.

10 Claims, 5 Drawing Sheets

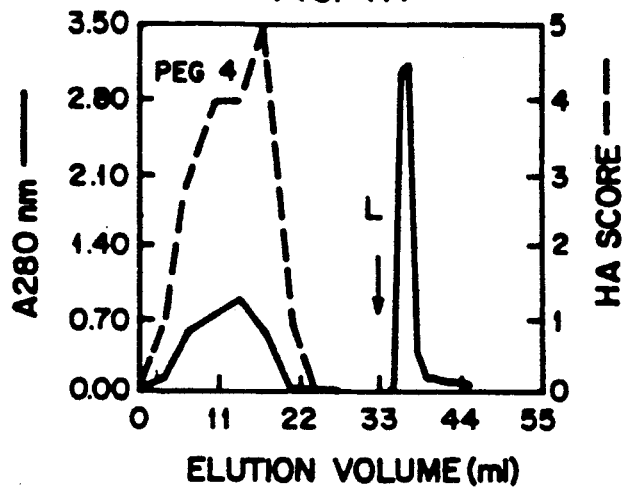
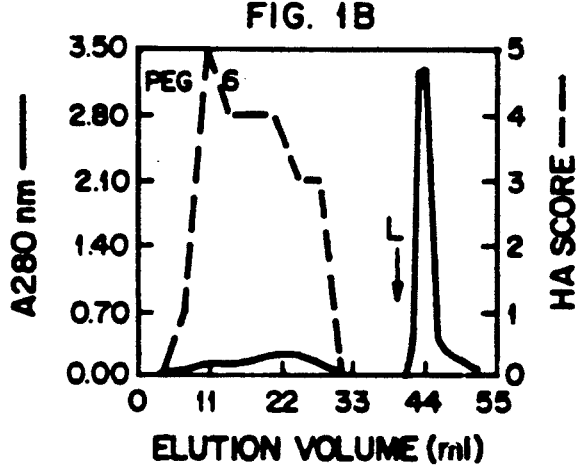
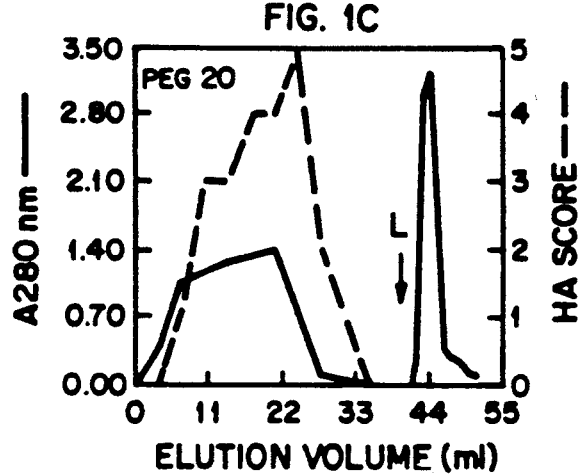

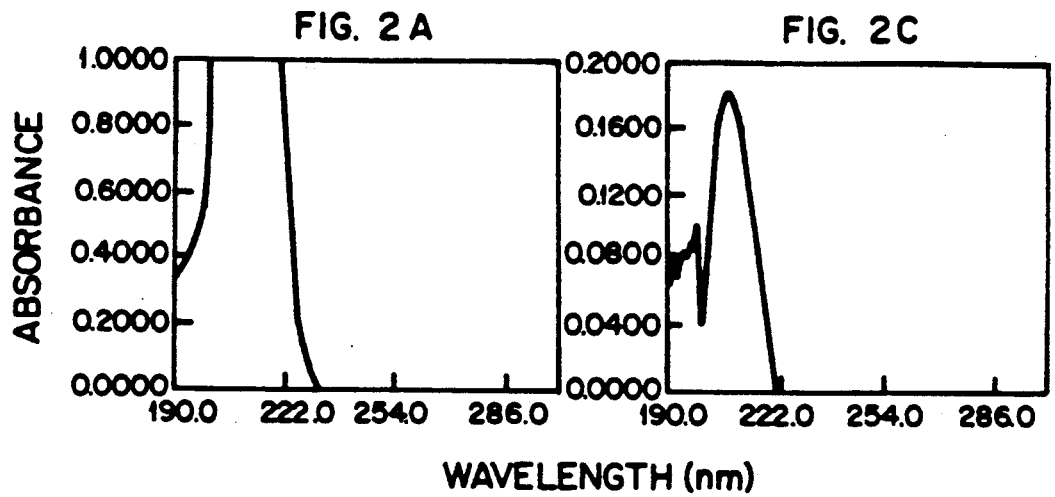
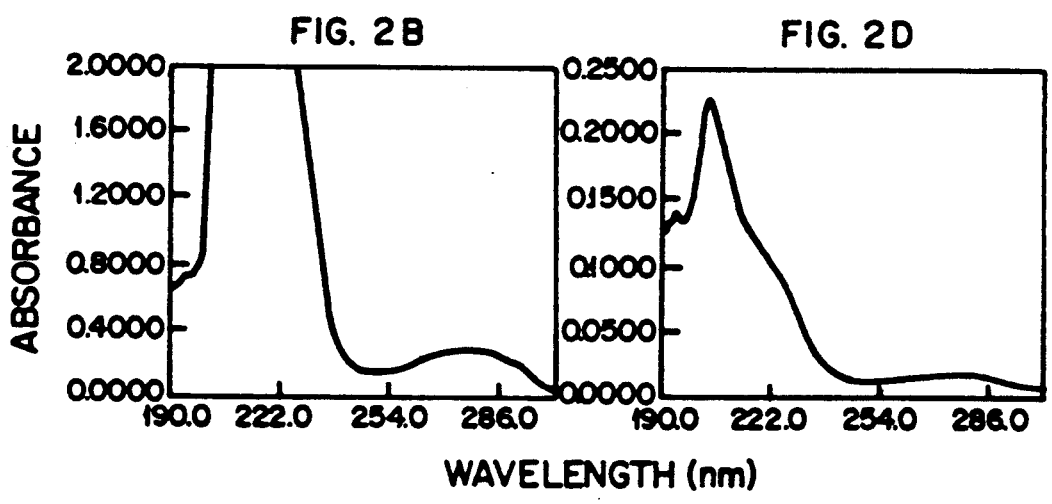

SYNTHESIS AND UTILIZATION OF CARBOHYDRATE-BINDING POLYMER-LECTIN CONJUGATES

This invention was made with government support under grant R01CA42584 awarded by the National Institutes of Health. The government has certain rights in the invention.

This application is a continuation-in-part of U.S. Ser. No. 690,641 filed Apr. 24, 1991, now abandoned, which is herein incorporated by reference.

FIELD OF THE INVENTION

The present invention relates generally to the use of lectins as therapeutic and diagnostic reagents and, more particularly, to polymer-lectin conjugates for use as immune modulators or targeting agents.

BACKGROUND OF THE INVENTION

Lectins are proteins derived from plant, animal, or microbial sources which have specific carbohydrate-binding activity. Because of their binding specificity for sugars and oligosaccharides, lectins have become useful reagents in the study of the biology and biochemistry of glycoconjugates in vitro (Rhodes et al., 1988, Digest. Dis. Sci., 33:1359-1363; and Green and Baenziger, 1989, Trends Biochem Sci., 14:168-171), and for the analysis of cellular components of the mammalian immune system (Smith, 1972, Transplant Rev., 11:179-216; and MacDonald and Natoholz, 1986, Ann. Rev. Cell. Biol., 2:231-254). The interaction of lectins with surface glYcoproteins of various cells of the immune system induce or inhibit a variety of responses in vitro which are indicative of cellular functions in vivo. For example, lectins can induce mitogenesis of T-lymphocytes (Favero et al., 1988, Cell. Immunol., 142:4401-4406) and induce synthesis and secretion of a variety of cytokines which are proteins involved in the regulation of immune responses (Miyajima et al., 1988, FASEB J., 2:2462-2473; and Taniguchi, 1988, Ann. Rev. Immunol. 6:439-464).

Many lectins have the potential for being powerful therapeutic and diagnostic reagents in vivo due to their carbohydrate-binding activity and specificity. Numerous lectins have been identified which could be screened for these purposes (Sharon and Lis, 1987, Tends Biochem. Sci. 12:488-491). However, principal factors which limit the development of lectins for in vivo use include their inherent toxicity, their potential to elicit an immunogenic response, and the short half-life of these substances in the circulatory system. In particular, an immune response against the lectins would enhance the destruction and clearance of subsequent introductions of the lectin, in addition to the possibility of causing an allergic reaction.

An inert water-soluble polymer may be conjugated to proteins to alter their properties (Inada et al. 1988, Trends Biotech. 6:131-134). The reduction in toxicity, immunogenicity, and clearance rate of certain polymer-protein conjugates has led to using polymer conjugation as a drug delivery system (Krieger, 1990, Chem. Eng. News, 68:38-40). For example, U.S. Pat. No. 4,179,337, discloses a process for coupling polypeptides, including enzymes and hormones, to polymers such as PEG. The resulting PEG-polypeptide conjugates are substantially non-immunogenic and retain some of the desired physiological activity of the base polypeptide when injected into the mammalian circulatory system.

U.S. Pat. No. 4,791,192 discloses a chemically modified protein which comprises an islet-activating protein produced by bacteria belonging to the genus Bordetella and a polyethylene glycol moiety bound with a primary amino group of the islet-activating protein.

U.S. Pat. No. 4,496,689, discloses a process for producing covalent conjugates formed by the chemical coupling reaction of the blood plasma glycoprotein, alpha-1-proteinase inhibitor, with an "activated" water soluble polymer, such as PEG. The conjugates are used in a method for treating pulmonary emphysema and respiratory distress syndrome.

Although conjugation of proteins to water-soluble polymers has been described in the prior art, it cannot be expected that the carbohydrate-binding activity of lectins can be retained after coupling because of potential steric hindrances involved in conjugation. Typically modification, such as by conjugation, of lectins involves covalent coupling between constituents of one or more functional groups of the modifying agent and one or more amino acids of the particular lectin. Thus, modification of lectins can result in concomitant loss of bioactivity, i.e. carbohydrate-binding activity, when amino acid residues of the lectin affected by the modification are amino acids which are necessary for bioactivity. The prior art fails to disclose a method which overcomes the problem of loss of carbohydrate-binding activity from modification of the lectin. Therefore, there exists a need for a method for predictably producing a water-soluble polymer-lectin conjugate that retains carbohydrate-binding activity subsequent to conjugation.

Additionally, lectins have been unable to achieve their potential for being biological response modifier in vivo because of their toxicity, immunogenicity and rapid clearance. Therefore, a need exists for carbohydrate-binding lectin derivatives which may be useful as therapeutic and diagnostic reagents in vivo and have reduced toxicity and immunogenicity with extended biologically active lifetime in vivo.

OBJECTS AND SUMMARY OF THE INVENTION

It is therefore, the primary object of the present invention to provide a carbohydrate-binding lectin derivative useful as a therapeutic and diagnostic reagent in vivo.

Another object of the present invention is to provide such a lectin derivative which has attenuated toxicity and immunogenicity.

Another object of the present invention is to provide such a lectin derivative comprised of the conjugate PEG-*Ricinus communis* agglutinin I.

Another object of the present invention is to provide such a lectin derivative which can be used in vivo as a biological response modifier of the immune system or as a targeting agent.

Another object of the present invention is to provide a process for preparing such a lectin derivative.

The present invention provides a process for preparing a carbohydrate-binding lectin derivative comprising isolating the lectin from a plant, animal or microbial origin, coupling the lectin to a water-soluble polymer having a molecular size of from about 1,000 to about 20,000 daltons, and substantially purifying the polymer-lectin conjugate from unconjugated lectin. The polymer may comprise a straight chain-polymer such as polyethylene glycol, polypropylene glycol, or cyclodextrin. The lectin may be coupled to the polymer by activating the polymer with a coupling agent such as 1,1'-carbonyldiimidazole or cyanuric chloride, or via an amine-reactive or thiol-reactive cross-linking agent.

The lectin derivative prepared in accordance with the process of the present invention is biocompatible, biologically active and expected to be substantially non-immunogenic, thus having potential for therapeutic application.

BRIEF DESCRIPTION OF THE FIGURES

FIG. 1A is a graph illustrating affinity chromatography of PEG 4-*Ricinus communis* agglutinin I conjugate (RCAI) on acid-treated Sepharose 6B.

FIG. 1B is a graph illustrating affinity chromatography of PEG 6-RCAI conjugate on acid-treated Sepharose 6B.

FIG. 1C is a graph illustrating affinity chromatography of PEG 20-RCAI conjugate on acid-treated Sepharose 6B.

FIG. 2A is a graph illustrating the UV spectra of 1,1'-carbonyldiimidiazole (at 0.10 mg/ml).

FIG. 2B is a graph illustrating the UV spectra of RCAI (at 0.25 mg/ml).

FIG. 2C is a graph illustrating the UV spectra of 1,1'-carbonyldiimidiazole (at 0.004 mg/ml).

FIG. 2D is a graph illustrating the UV spectra of RCAI (at 0.020 mg/ml).

FIG. 6 is a photograph of a SDS-PAGE of PEG-*Ricinus communis* agglutinin I.

DETAILED DESCRIPTION OF THE INVENTION

Figure 3A:
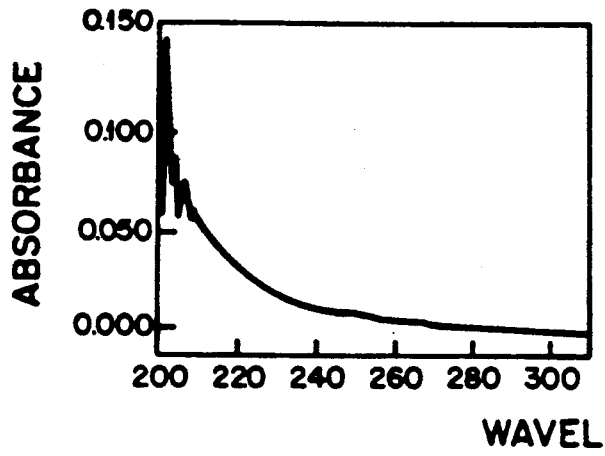
FIG. 3A is a graph illustrating UV spectra of PEG 4 (at 5 mg/ml).

The method of the present invention discloses conjugation of a lectin in the presence of the specific carbohydrate for which it has affinity. By including that carbohydrate in the reaction, carbohydrate bound in the carbohydrate-binding site of the lectin prevents coupling between the polymer and any amino groups contained within the carbohydrate-binding site of the lectin which would otherwise be available to be coupled to the polymer. The carbohydrate is then removed from the conjugate by dialysis or by gel filtration and the conjugate is subsequently purified by affinity chromatography. Thus, the addition to the conjugation reaction of the specific carbohydrate for which the lectin has affinity, overcomes the problem of steric hinderances encountered in the conjunction of lectin and polymer. Lectins useful in the conjugates of the present invention include those lectins that bind carbohydrates of human cell-surface receptors. A partial list of lectins containing this desired activity, along with their respective carbohydrate for which they have affinity and which is present in a conjuction reaction in accordance with the present invention, is included in Table I. Persons skilled in the art will know of other lectins with diagnostic or therapeutic applications which would be desirably conjugated in accordance with the present invention.

TABLE I

| Lectin | Carbohydrate |
|---|---|
| Concanavalin A | methyl-α-D-mannopyranoside |
| green pea (*Pisum sativum*) | methyl-α-D-mannopyranoside |
| lentil (*Lens culinaris*) | methyl-α-D-mannopyranoside |
| peanut (*Arachis hypogaea*) | lactose or disaccharide D-galactose linked to N-Acetyl-D-galactosamine |
| soybean (*Glycine max*) | lactose or disaccharide D-galactose linked to N-Acetyl-D-galactosamine |
| *Wisteria floribunda* agglutinin and mitogen | lactose or disaccharide D-galactose linked to N-Acetyl-D-galactosamine |
| *Bauhinia purpurea alba* | D-galactose or N-Acetyl-D-galactosamine |
| *Sophora japonica* | lactose or D-galactose linked to N-Acetyl-D-glucosamine |
| *Dolichos biflorus* | N-Acetyl-D-galactosamine |
| lima bean (*Phaseolus lunatus*) | D-galactose linked to N-Acetyl-D-galactosamine |
| *Erythrina cristagalli* | lactose or D-galactose linked to N-Acetyl-D-glucosamine |
| *Maclura pomifera* | D-Galactose linked to N-Acetyl-D-galactosamine |
| sweet pea (*Lathyrus odoratus*) | methyl-α-D-mannopyranoside |
| *Ricinus communis* Agglutinin I | lactose |

Various lectin derivatives may be synthesized in accordance with the present invention resulting in derivatives having potential for therapeutic application. The derivatives may be prepared by utilizing the methods of the present invention wherein the particular lectin and its corresponding carbohydrate are selected from Table I. As an illustrative example, synthesis and carbohydrate-binding activity of a lectin derivative comprising polyethylene glycol- *Ricinus communis* agglutinin I conjugate (hereinafter PEG-RCAI) is disclosed herein. The different PEG conjugates described herein, PEG 4 (MW 3350), 6 (MW 8000) and 20 (MW 20,000), were separated into fractions differing in their carbohydrate-binding affinity, i.e., for acid-treated Sepharose. Each fraction was heterodisperse with respect to molecular weight indicating that the ratio of PEG/molecule of RCAI was highly variable. The present invention will become more apparent to one skilled in the art with reference to the following examples.

EXAMPLE I

Isolation of Ricinus communis Agglutinin I

*Ricinus communis* agglutinin I (RCAI) was isolated using affinity chromatography with acid-treated Sepharose 6B in accordance with the method described by Allen and Johnson, 1976, Carbohydr. Res. 50:121–131. Ground castor beans (*Ricinus communis*) were extracted at 4° C. with a buffer of PBS (0.15M NaCl, 15 mM Na$_3$PO$_4$, 0.05% NaN$_3$, pH 7.0) at a ratio of 100 g of beans per liter PBS. The extract was then centrifuged and subjected to ammonium sulfate precipitation. Acid-treated Sepharose 6B was prepared by washing the gel with 0.2M HCl, adding the acid-washed gel (50 ml) to 0.2M HCl (100 ml), and gently shaking the suspension in a 50° waterbath for 2 to 3.5 hours. Prior to use, the acid-treated Sepharose 6B was washed with pBS. The 0.4–0.6 fraction from ammonium sulfate precipitation was applied to an affinity column containing the acid-treated Sepharose 6B. Chromatography of the Ricinus lectins at 24° C. on acid treated Sepharose 6B resulted in good binding of both agglutinins I and II, and both agglutinins co-eluted in 0.1 M lactose. Gel filtration on Sephadex G-150 (Pharmacia) was used to separate the agglutinins.

EXAMPLE II

Conjugation of PEG to RCAI.

PEG was activated with 1,1'-carbonyldiimidazole (CDI) by first dissolving PEG in dioxane at 37° at a concentration of 50 mM (PEG 4, and pEG 6), or 5 mM (PEG 20), and then adding 1,1'-carbonyldiimidazole (CDI) to a final concentration of 500 mM; incubating the solution at 37° for 2 hours with stirring; followed by dialyzing in water at 4° C. After dialysis, the solutions were lyophilized. The resultant powder constituted "activated PEG". In some experiments, activated PEG was passed through a column of Sephadex G-25 (Pharmacia) equilibrated with H$_2$O as an alternative to dialysis. PEG used includes PEG 4 (MW 3350), PEG 6 (MW 8,000) and PEG 20 (MW 20,000) obtained from Fisher Scientific, Rochester, New York.

To conjugate PEG 20 to RCAI, 0.5 g of activated PEG 20 was dissolved in 10 mM Na$_2$B$_4$O$_7$, pH 8.5 to a volume of 2.5 ml. 15 mg of RCAI and 90 mg of lactose were added to the solution. The solution was mixed for 72 hours at 4° C. PEG 6 was conjugated to RCAI by dissolving 0.25 g of activated PEG 6, 6.2 mg of RCAI 37 mg of lactose in 1.0 ml of 10 mM Na$_2$B$_4$O$_7$, pH 8.5. The solution was stirred for 72 hours at 4° C. Alternatively, conjugation may be carried out as described for PEG 20. PEG 4 was conjugated to RCAI by dissolving 0.27 g of activated PEG 4 in 2.2 ml of Na$_2$B$_4$O$_7$/0.1 M lactose, pH 8.5, containing 12.5 mg RCAI. The solution was stirred for 72 hours at 4° C.

Lactose was removed from the conjugates using standard dialysis tubing obtained from Fisher Scientific by dialyzing against 0.1M NaCl/0.05 PO$_4$/0.05% NaN$_3$, pH 7.3 (PBS), or by passage through a Bio Gel P-2 column (BioRad) equilibrated with 0.1M NaCl/0.05M Tris/0.05% NaN$_3$, pH 7.3 (TBS).

EXAMPLE III

Assessment of the carbohydrate-binding activity of the PEG-RCAI conjugates

Figure 3C:
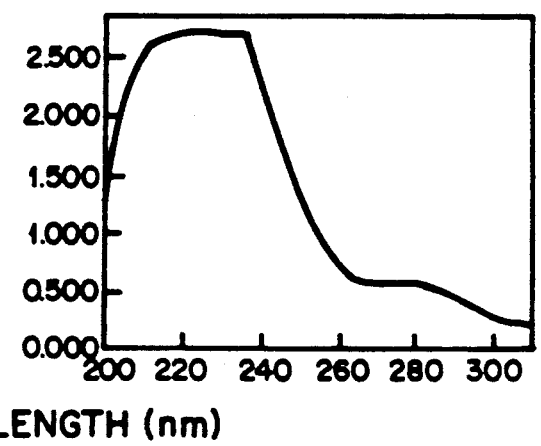
FIG. 3C is a graph illustrating UV spectra of non-bound PEG 4-RCAI conjugate (0.7 mg RCAI/ml).
Figure 3B:
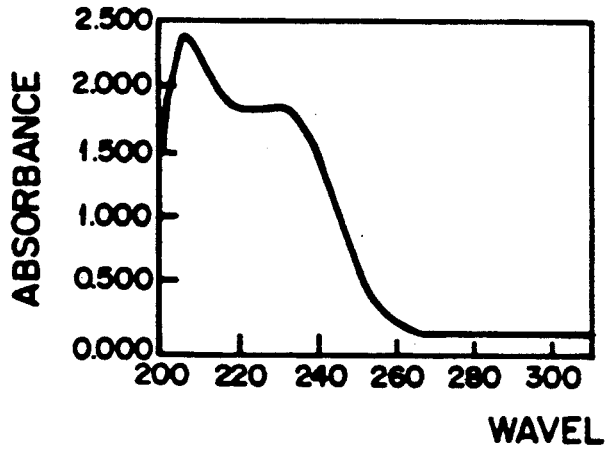
FIG. 3B is a graph illustrating UV spectra of activated PEG 4 (at 1.25 mg/ml).
Figure 3D:
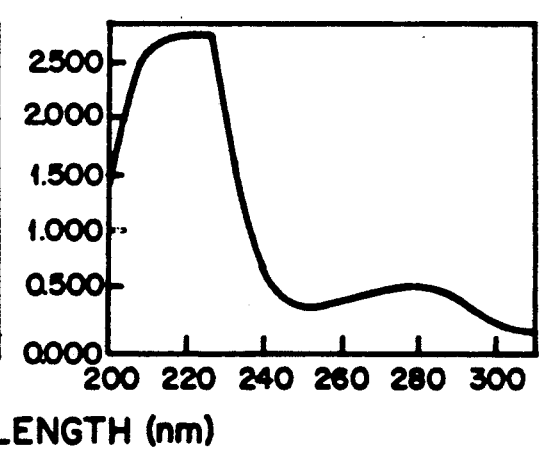
FIG. 3D is a graph illustrating UV spectra of lactose-eluted PEG 4-RCAI conjugate (0.54 mg RCAI/ml).

The conjugate preparations were assessed for their ability to bind carbohydrates using affinity chromatography on acid-treated Sepherose 6B following procedures as outlined in Example I. Sepharose 6B was incubated with 0.2 M HCl for 2-3.5 hours in a 50° C. shaking water bath, then washed a final time with PBS. Acid treatment increased the binding affinity and capacity for lectin-Sepharose interaction. With reference to FIG. 1, each type of PEG (FIG. 1A- PEC 4-RCAI; FIG. 1B- PEG 6-RCAI; FIG. 1C- PEG 20-RCAI) was conjugate was separated into two pools based on its binding affinity for acid-treated Sepharose. After loading the affinity columns (bed volume=3.5 ml), the non-binding pool washed off the column with PBS and the bound pool was eluted with 0.1M lactose (L). The chromatography was carried out at 4° C. Fractions were assayed for protein ($A_{280}$) and hemagglutinating activity (Allen et al., 1977, Immunol. Comm. 6:585-602). The load volume was 15, 25 and 20 ml for PEG 4, PEG 6 and PEG 20 conjugates., respectively. The lactose-eluted pools contained 40%, 72% and 26% of the recovered protein for PEG 4, PEG 6 and PEG 20 conjugates, respectively, (Table 1).

The results of affinity chromatography suggest that some of the conjugates had hindered carbohydrate-binding sites and therefore did not bind to acid-treated Sepharose. Steric considerations suggest that conjugation of lectins with low molecular weight PEG would result in less interference with carbohydrate binding. Comparison of the affinity chromatography results showed than a larger proportion of the PEG 4 and PEG 6 conjugates were capable of binding acid-treated Sepharose compared to the PEG 20 conjugate.

EXAMPLE IV

Assessment of Hemagglutinating activity.

Hemagglutination assays were carried out in microtiter plates with 2% rabbit erythrocytes in PBS. The individual pools from the acid-treated Sepharose column were concentrated with Centricon 10 devices (Amicon, Danvers, MA.), then dialyzed against 0.15 M NaCl. Assays were performed by incubating the pooled, fractions (50 ul) from chromatography with 25 ul of the erythrocytes suspension at room temperature for at least 2 hours. The hemagglutinating activity of the dialyzed pools was quantitated by two-fold serial titration and the results are shown in Table II. With reference to Table II, the specific hemagglutinating activity of the non-bound pools for PEG 6 and PEG 20 conjugates was less than that for the bound pools. All PEG conjugate fractions had a specific hemagglutinating activity less than that for free RCAI.

EXAMPLE V

Assessment of the conjugates

Efficiency of PEG-RCAI conjugation, i.e. the presence of PEG and/or RCAI in the conjugate fractions, was assessed by UV spectra (Perkin-Elmer Lamda 4A spectrophotometer) for the conjugates, PEG, activated PEG, RCAI, and CDI. CDI was dissolved in 0.15 M NaCl. RCAI was dialysed against 0.15 M NaCl prior to analysis. As shown in the graphs of FIG. 2, FIG. 2A represents CDI, 0.10 mg/ml; FIG. 2B represents RCAI, 0.25 mg/ml; FIG. 2C represents CDI, 0.004 mg/ml; and FIG. 2D represents RCAI, 0.020 mg/ml. CDI had a major absorption peak at about 209 nm. At low CDI concentration, a poorly defined absorption peak at about 200 nm was distinguished. No absorption above around 238 nm was detected. The UV spectrum for RCAI was typical of a glycoprotein, i.e. an absorption peak at about 280 nm was present. An absorption peak at about 202 nm with a shoulder at about 222 nm which is typical of absorption due to peptide bonds and glycosidally-bound carbohydrate was also present.

The UV spectra for PEG 4 and its derivatives are shown in FIG. 3. All samples were dialysed against 0.15 NaCl prior to analysis. As shown in the graphs of FIG. 3, FIG. 3A represents PEG 4, 5 mg/ml; FIG. 3B represents activated PEG 4, 1.25 mg/ml; FIG. 3C represents non-bound PEG 4-RCAI conjugate, 0.7 mg RCAI/ml; and FIG. 3D represents lactose-eluted PEG 4-RCAI conjugate, 0.54 mg RCAI/ml. At high concentrations, PEG 4 showed a weak poorly defined absorption at about 200-210 nm. Activated PEG 4 showed a strong absorption peak at about 206 nm and a slightly weaker one at about 230 nm. PEG 4-RCAI conjugate which did not bind to acid-treated Sepharose, but contained hemagglutinating activity, showed a major absorption peak in the short UV range which was characteristic of activated PEG 4, and a weaker absorption peak at about 280 nm which was characteristic of RCAI. PEG 4-RCAI conjugate which retained carbohydrate binding activity (bound to the affinity column) and which was eluted with lactose, had an absorption spectrum similar to non-bound conjugate. However, the bound conjugate appeared to have less absorption in the short UV relative to that at about 280 nm when compared to the non-bound fraction.

Figure 4A:
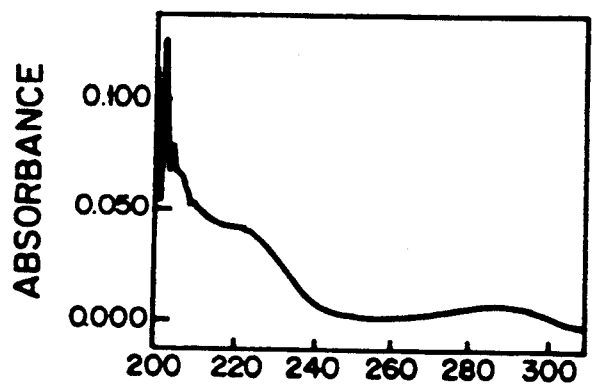
FIG. 4A is a graph illustrating UV spectra of PEG 6 (at 5 mg/ml).
Figure 4C:
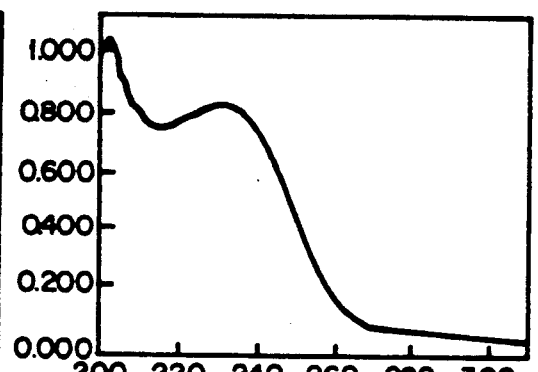
FIG. 4C is a graph illustrating UV spectra of non-bound PEG 6-RCAI conjugate (0.07 mg RCAI/ml).
Figure 4B:
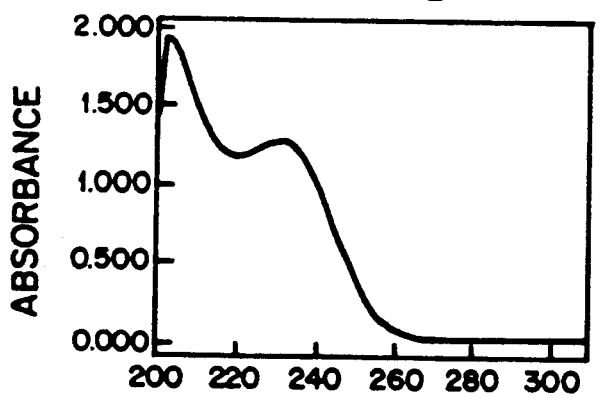
FIG. 4B is a graph illustrating UV spectra of activated PEG 6 (at 2.5 mg/ml).
Figure 4D:
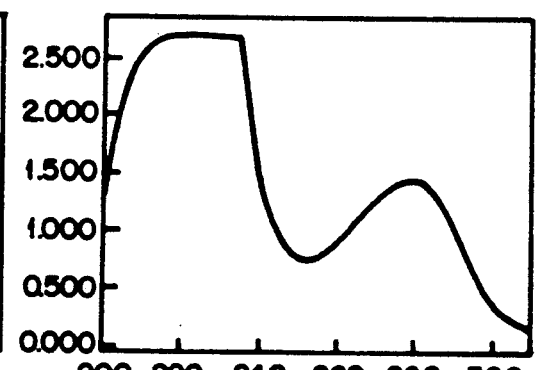
FIG. 4D is a graph illustrating UV spectra of lactose-eluted PEG 6-RCAI conjugate (1.27 mg RCAI/ml).

The UV spectra for PEG 6 and its derivatives are shown in FIG. 4. With reference to FIG. 4, all samples were dialysed against 0.15 M NaCl prior to analysis. As shown in the graphs of FIG. 4, FIG. 4A represents PEG 6, 5 mg/ml; FIG. 4B represents activated PEG 6, 2.5 mg/ml; FIG. 4C represents non-bound PEG 6-RCAI conjugate, 0.07 mg RCAI/ml; and FIG. 4D represents lactose-eluted PEG 6-RCAI conjugate, 1.27 mg RCAI/ml. Native and activated PEG 6 had absorption spectra similar to those for PEG 4. PEG 6-RCAI conjugate which did not bind to the affinity column lacked a sufficient amount of protein to generate an absorption peak at about 280 nm. However, the UV absorption spectrum for the conjugate which bound to acid-treated Sepharose showed a prominent absorption peak at about 280 nm due to the presence of RCAI.

Figure 5A:
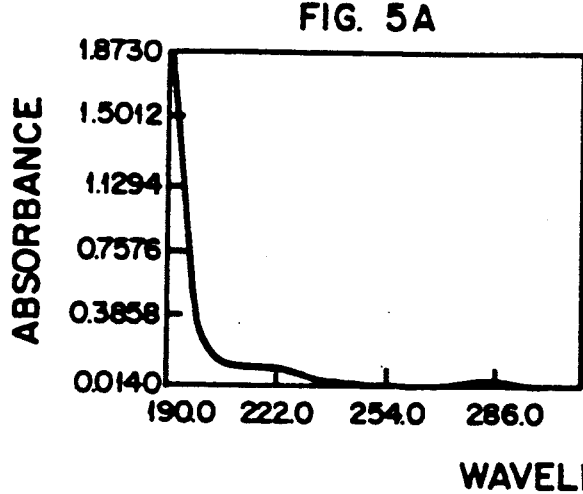
FIG. 5A is a graph illustrating UV spectra of PEG 20 (at 5 mg/ml).
Figure 5C:
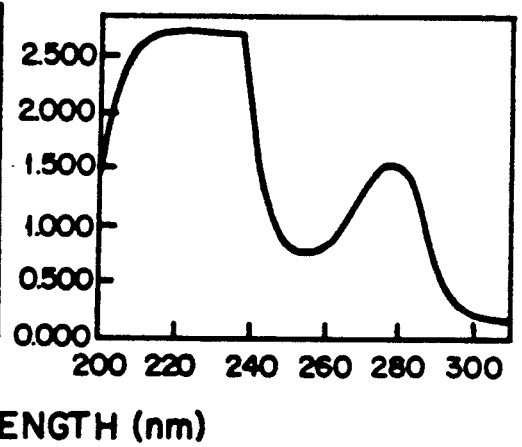
FIG. 5C is a graph illustrating UV spectra of non-bound PEG 20-RCAI conjugate (1.54 mg RCAI/ml).
Figure 5B:
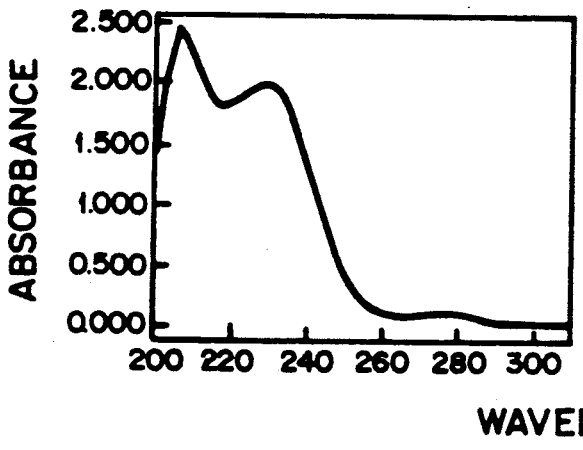
FIG. 5B is a graph illustrating UV spectra of activated PEG 20 at 2.5 mg/ml).
Figure 5D:
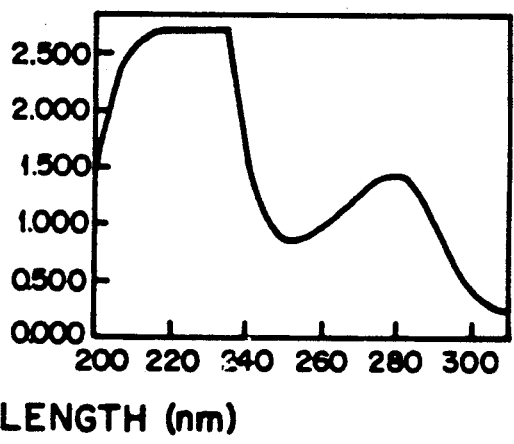
FIG. 5D is a graph illustrating UV spectra of lactose-eluted PEG 20-RCAI conjugate (1.39 mg RCAI/ml).

With reference to FIG. 5, the UV spectra for PEG 20 and its derivatives are shown. All samples were dialysed against 0.15 NaCl prior to analysis. As shown in the graphs of FIG. 5, FIG. 5A represents PEG 20, 5 mg/ml; FIG. 5B represents activated PEG 20, 2.5 mg/ml, FIG. 6 (represents non-bound PEG 20-RCAI conjugate, 1.54 mg RCAI/ml; and FIG. 5D represents lactose-eluted PEG 20-RCAI conjugate, 1.39 mg RCAI/ml. In contrast to PEG 4 and 6, native PEG 20 had a major absorption peak at about 192 nm. Activated PEG 20 had a UV absorption spectrum similar to those for activated PEG 4 and 6. The PEG 20 conjugate fraction which did not bind to the affinity column had a major absorption peak at about 280 nm which demonstrated the presence of RCAI in the fraction. The PEG-conjugate fraction which was eluted from the affinity column with lactose had a UV absorption spectrum similar to the non-bound fraction.

Conjugation was also evaluated by assaying the fractions for free amino groups by reaction with trinitrobenzenesulfonate (TNBS), using lysine as a standard, in accordance with the method of Habeeb, 1966, Analyt. Bichem. 14:328-336. The hemagglutinating activity and free amine content of PEG-RCAI conjugate pools from affinity chromatography are shown in Table III. The PEG conjugates which bound to the affinity column had a higher content of free amines than the corresponding non-bound pools. This suggests that the non-bound pools were more highly conjugated with PEG than the bound pools. Yet, the non-bound pools retained reactivity with high-affinity receptors as shown by the hemagglutination assays.

TABLE II

| Sample | % A280[a] | A280[b] | HA Titer | Titer/A280 |
|---|---|---|---|---|
| PEG 20 nonbound | 74 | 1.88 | 32 | 17 |
| PEG 20 bound | 26 | 1.69 | 128 | 76 |
| PEG 6 nonbound | 28 | 0.080 | 2 | 25 |
| PEG 6 bound | 72 | 1.546 | 128 | 83 |
| PEG 4 nonbound | 60 | 0.868 | 16 | 18 |
| PEG 4 bound | 40 | 0.657 | 16 | 24 |
| RCAI |  | 6.38 | 1024 | 162 |

[a]Relative proportion of A280 nm units in non-bound and bound fractions.
[b]A280 nm of samples titered for hemagglutinating activity.

TABLE III

| Sample | μg protein/ml[a] | μmole amine/μg protein[b] |
|---|---|---|
| PEG 20 nonbound | 3.3 | ND[c] |
| PEG 20 bound | 1.5 | $4.20 \times 10^{-4}$ |
| PEG 6 nonbound | 5.0 | ND |
| PEG 6 bound | 1.5 | $7.20 \times 10^{-4}$ |
| PEG 4 nonbound | 3.7 | $1.02 \times 10^{-4}$ |
| PEG 4 bound | 3.5 | $8.65 \times 10^{-4}$ |

[a]Protein concentration, determined by dye-binding assay, at hemagglutination endpoint.
[b]Amine content determined by the TNBS reation.
[c]None detected.

EXAMPLE VI

Cyclodextrin-lectin coupling

Other polymers may be coupled to lectins to reduce immunogenicity and prolong in-vivo half life. One such polymer is β-cyclodextrin, comprised of seven cyclic glucosyl moieties. This conjugate may be used for the transport in-vivo of other compounds that may be non-covalently complexed with or covalently linked to β-cyclodextrin. Conjugation of β-cyclodextrin to RCAI may proceed with 6[A]-amino-6[A]-deoxy- β-cyclodextrin (NH-cyclodextrin) as the starting compound. This compound is quite soluble and can be further derivatized to possess carboxyl and thiol functional groups. The amino derivative of β-cyclodextrin is commercially available, or may be chemically synthesized. The conjugation of β-cyclodextrin to lectin may be accomplished by utilizing several of the coupling agents known in the art, as exemplified by the following:

6.1 Conjugation of NH-cyclodextrin to Lectin via glutaraldehyde

One embodiment for conjugation of NH-cyclodextrin to lectin may involve coupling with glutaraldehyde. This reagent is used for the covalent coupling of compounds containing primary and secondary amino groups. In an example of this embodiment, coupling may be accomplished by incubating RCAI and NH-cyclodextrin in phosphate buffered saline (PBS/0.1% glutaraldehyde/ 0.1M lactose for 17 hours at 4° C. Then 0.1 M Tris, pH7.3 may be added to the mixture, followed by dialysis against 0.01M Tris. The conjugate may then be subjected to affinity chromatography through a column of acid-treated Sepharose 6B. Protein concentration and hemagglutinating activity of the fractions may be assayed for the NH-cyclodextrin-RCAI conjugates as described in Examples IV and V. Washthrough and saccharide-eluted fractions containing protein may also be assayed by SDS-polyacrylamide gel electrophoresis. Appropriate fractions containing protein may be pooled for dialysis followed by analyses by protein, neutral sugar, and hemagglutination assays. Substitution of lectin amino groups may be determined by the TNBS reaction.

6.2 Conjugation of NH-cyclodextrin to Lectin via Bis(sulfosuccinimidyl) suberate (BS)

In another embodiment, the amino groups may be homocrosslinked with BS, a water soluble amine-reactive crosslinker that has been used in studies probing ligand-receptor interactions (Staros, 1982, Biochemistry 21: 3950–3955). An example of a procedure for crosslinking lectin to BS involves first equilibrating RCAI in in 50 mM sodium phosphate, pH 7.4 containing 0.1M lactose. Reagent concentrations of BS, from about 0.20 mM to about 2.0 mM in 50 mM sodium phosphate, pH 7.4 is added per mg/ml of lectin and incubated for 30 minutes at room temperature. The reaction is then quenched by the addition of 1/6 volume of 50 mM ethanolamine in 50 mM sodium phosphate pH 7.4. Lactose may be removed by dialysis or by gel filtration. The conjugates may then be isolated by affinity chromatography.

6.3 Conjugation of NH-cyclodextrin to Lectin via 1-ethyl-3-(3-dimethylaminopropyl) carbodiimide (EDC) coupling Conjugation via amide bond formation, between the NH group of cylodextrin and COOH groups of lectin, may be carried out, for example, by reaction of RCAI and NH-cyclodextrin in the presence of EDC and N-hydroxysulfosuccinimide (Sulfo-NHS) (Staros et al., 1986, Anal. Biochem. 156:220–222) and 0.1M lactose in an overnight incubation at room temperature. Lactose is removed by dialysis or gel filtration and the conjugate is purified by affinity chromatography.

A variation of this procedure may involve prior succinylation of the amino group of NH-cyclodextrin in aqueous base to introduce a carboxyl group. EDC coupling will then be carried out resulting in amide bond formation between the amino groups of the lectin and carboxylated cyclodextrin. An alternative to reaction with succinic anhydride may be reaction with citraconic anhydride to generate a potentially more acid-labile crosslinkage. An acid-labile linkage will be of interest when it is desirable to achieve intracellular bond cleavage to yield free cyclodextrin and lectin. This cleavage may occur in the acidic environment of lysosomes.

6.4 Conjugation of NH-cyclodextrin to lectin via 4-succinimidyloxycarbonyl-o-methyl-o-(2-pyridldithio)toluene(SMPT) and N-succinimidyl3-(2-pvridvldithio) proorionate (SPDP)

SMPT and SPDP may be used as reagents to conjugate NH-cyclodextrin to lectin via disulfide bonds. For conjugation of proteins using these reagents, typically, amino groups of one protein may be reacted with SMPT or SPDP in a borate buffer to yield a disulfide-containing derivative (Thorpe et al., 1987 Cancer Research 47:5924–5931). A second protein, such as lectin comprising RCAI, containing free sulfhydryl groups may then be reacted with the activated protein in the presence of 0.1M lactose. Disulfide bond exchange occurs to yield free pyridine-2-thione and conjugated proteins linked by disulfide bonds. The lactose is removed by dialysis or gel filtration and the resulting conjugate is purified by affinity chromatography. A variation of this coupling procedure may be used whereby a free sulfhydryl may be introduced into NH-cyclodextrin or lectin by reaction with SMBT or SPDP followed by reduction with DDT. Conditions, as described by Carlsson et al. (Biochem. Journal 173:723≧737, 1978), may be chosen to minimize reduction of endogenous protein disulfide bonds. Similarly, activated cyclodextrin or lectin, but not reduced, may be allowed to undergo disulfide bond exchange with the free sulfhydryl introduced into the other member of the conjugate.

EXAMPLE VII

Purification and utilization of the polymer-lectin conjugates

It may be desirable to further purify polymer-lectin conjugates before utilizing the derivatives in vivo as a diagnostic or therapeutic agent. For example, if in assessing the efficiency of conjugation (as described in Example V) unconjugated lectin was detected, it would be desirable to remove from the polymer-lectin conjugate the unconjugated lectin which possesses immunogenic and toxic properties. Methods known in the art, such as gel exclusion chromatography, which exploit differences in molecular size to separate species may be used to separate lectin from lectin coupled to a polymer. Additionally, there may exist a situation where within the polymer-lectin conjugate exists a species of conjugate that fails to bind to its particular carbohydrate, i.e. if the carbohydrate concentration in the conjugation process is insufficient to bind all lectin present. Thus subsequent to the conjugation process, there may exist a species of polymer-lectin conjugate which lacks carbohydrate-binding activity wherein amino acids in the carbohydrate-binding portion of the lectin have been coupled to polymer. This species of polymer-lectin conjugate may be readily separated from functional polymer-lectin conjugate by virtue of methods known in the art, such as affinity chromatography, which exploit carbohydrate-binding ability or activity to separate species.

Once a pharmacologically-suitable preparation of polymer-lectin conjugate has been produced in accordance with the present invention, an effective amount of the lectin derivative may be administered to a human as a biological response modifier. In addition, the lectin derivative may be tagged, by methods known in the art, with a diagnostically-recognizable marker resulting in a preparation of lectin derivative which may be used for the in vivo detection of specific cell populations. Specific populations may be distinguishable from other cell populations by the particular cell-surface carbohydrates with which lectin derivatives may bind. Diagnostically-recognizable markers include, but are not limited to, radioactive or fluorescent markers which can be detected by non-invasive diagnostic procedures.

It is understood that the embodiments of the present invention as described herein are for purposes of illustration only and, not limitation, and any changes or modifications as will become apparent to one of ordinary skill in the art from the foregoing description and accompanying figures are intended to be included within the scope of the appended claims. For example, although polyethylene glycol, polypropylene glycol and cyclodextrin are the preferred polymers, other straight or branched chain polymers which do not generate an immunogenic response could be used herein in synthesizing the lectin derivatives of the present invention. Furthermore, alternate affinity absorbents and gradient elution techniques may yield more homogenous conjugate fractions for analysis. The polymer-lectin conjugates produced herein may have other therapeutic applications other than for use as biological response modifiers.

We claim:

1. A process for preparing a carbohydrate-binding lectin derivative comprising:
   (a) isolating a lectin of plant, animal, or microbial origin from other molecules from said origin by utilizing the carbohydrate-binding affinity of said lectin;
   (b) covalently coupling said lectin via amino groups of said lectin and in the presence of a carbohydrate for which the lectin has binding affinity, to a water soluble polymer selected from the group consisting of polyethylene glycol, polypropylene glycol and cyclodextrin having a molecular size of from about 1,000 to about 20,000 daltons;
   (c) removing the carbohydrate from the polymer-lectin conjugate of step (b) by a process selected from the group consisting of dialysis and gel filtration;
   (d) purifying the polymer-lectin conjugate from unconjugated lectin having immunogenic and toxic properties by chromatographic means which separates by differences in size, and charge;
   (e) purifying the polymer-lectin conjugate having carbohydrate-binding activity from polymer-lectin conjugate lacking carbohydrate-binding activity by a means which separates by carbohydrate-binding activity comprising affinity chromatography with a carbohydrate for which the lectin has binding affinity, wherein after separation the polymer-lectin conjugate having binding activity is unbound from the carbohydrate by a process selected from the group consisting of dialysis and gel filtration; said purified polymer-lectin conjugate being biocompatible and retaining carbohydrate-binding activity.

2. The process of claim 1 wherein the lectin is selected from the group consisting of Concanavalin A, green pea, lentil, peanut, soybean, *Wisteria floribunda* agglutinin and mitogen, *Bauhinia purpurea alba*, *Sophora japonica*, *Dolichos biflorus*, lima bean, *Erythrina cristagalli*, *Maclura pomifera*, sweet pea, and *Ricinus communis* agglutinin I.

3. The process of claim 1, wherein said polymer is a straight chain polymer selected from the group consisting of polyethylene glycol and polypropylene glycol.

4. The process of claim 3, wherein said polyethylene glycol (pEG) is PEG 4 having a molecular weight of 3500.

5. The process of claim 3, wherein said polyethylene glycol (PEG) is PEG 6 having a molecular weight of 8,000.

6. The process of claim 3, wherein said polyethylene glycol (PEG) is PEG 20 having a molecular weight of 20,000.

7. The process of claim 2, wherein said coupling step in facilitated by activating said polymer with a coupling agent selected from the group consisting of 1,1'carbonyldiimidazole or cyanuric chloride.

8. The process of claim 2, wherein said lectin is *Ricinus communis* agglutinin I.

9. A polymer-lectin conjugate produced by the process of claim 1, said conjugate being biocompatible and retaining carbohydrate-binding activity.

10. The conjugate of claim 9, wherein the lectin is selected from the group consisting of Concanavalin A, green pea, lentil, peanut, soybean, *Wisteria floribunda* agglutinin and mitogen, *Bauhinia purpurea alba*, *SoDhora japonica*, *Dolichos biflorus*, lima bean, *Erythrina cristaqalli*, *Maclura pomifera*, sweet pea. and *Ricinus communis* agglutinin I.

* * * * *